United States Patent [19]

Gravrok et al.

[11] 4,165,230

[45] Aug. 21, 1979

[54] AGRICULTURAL SPRAY OILS CONTAINING ZINC DIALKYLDITHIOPHOSPHATES

[75] Inventors: Ralph E. Gravrok, Coral Gables, Fla.; Clarence A. L. Phillips, Ponte-a-Pierre, Trinidad and Tobago

[73] Assignee: Texaco Inc., White Plains, N.Y.

[21] Appl. No.: 926,993

[22] Filed: Jul. 21, 1978

[51] Int. Cl.$^2$ ............................................. A01N 17/08
[52] U.S. Cl. ................................. 71/127; 71/DIG. 1; 71/87; 424/358
[58] Field of Search .................... 71/127, 87, DIG. 1; 424/358

[56] References Cited

U.S. PATENT DOCUMENTS 3,097,088  7/1963  Reck et al. ............................. 71/127

OTHER PUBLICATIONS

Tucker, Ind. Eng. Chem., (1956), vol. 28, p. 458.

*Primary Examiner*—Catherine L. Mills
*Attorney, Agent, or Firm*—Thomas H. Whaley; Carl G. Ries; Henry W. Archer

[57] ABSTRACT

The phytotoxicity of conventional agricultural spray oils is reduced by the incorporation therein of between 0.10 and 0.25 weight/volume percent thereof of at least one zinc dialkyldithiophosphate wherein the alkyl group ranges from $C_3$ to $C_8$. The additive also provides zinc and phosphorus to the plants treated with such oils.

3 Claims, No Drawings

AGRICULTURAL SPRAY OILS CONTAINING ZINC DIALKYLDITHIOPHOSPHATES

BACKGROUND OF THE INVENTION

1. Field of the Invention

This invention relates to reducing the phytotoxicity of conventional horticultural petroleum spray oils by incorporation in such oils of zinc dialkyldithiophosphates.

Petroleum oils are used in agriculture as carriers or solvents for spraying pesticides (fungicides, insecticides, ovicides, etc.), herbicides, micronutrients and various types of chemical adjuvants. They are also used as agricultural spray oils in their own right, i.e., without additives, because of their natural herbicidal and pesticidal properties. They control a wide range of pests, for examples, Sigatoka disease in banana, earworm in sweet corn, Cercospora in sugar beet, and mites, aphids, scale insects in deciduous fruit trees, citrus and ornamentals. The main advantages of petroleum spray oils are their relative cheapness, their low health hazard and the apparent inability of fungi, insects and mites to develop strains resistant to them.

The properties required for an oil to perform efficiently as a carrier do not necessarily conflict with those required for an oil to act as a natural herbicidal or pesticidal spray oil. Indeed many commercial spray oils perform both functions. Present day conventional petroleum spray oils are derived from light lube oil distillates.

2. Statement of the Prior Art

The prior art to which this invention relates is already aware of U.S. Pat. No. 3,097,088 which relates to plant growth regulatory compositions consisting of spray oils containing primary amine salts of 3,6 endoxohydrophthalic acid. This art is also aware of the article by R. P. Tucker (Ind. Eng. Chem., 1956, 28, 458) which showed that the aromatic hydrocarbons are not toxic to the foliage of plants in a chemical sense until they are oxidized to oil soluble asphaltogenic acids. Similarly, it should be noted that coassigned copending U.S. application Ser. No. 835,280 filed Sept. 21, 1977, discloses the elimination or reduction of phytotoxicity of petroleum spray oils by the addition thereto of from 0.01 to 8 weight percent of N,N'-di-sec. butyl-p-phenylenediamine; phenyl-a-naphthyl amine; p,p'-dioctyldiphenylamine; diphenylamine, B-naphthylamine, 2-mercaptobenzothiazole, zinc dibutyl-dithio carbamate, sulfurized sperm oil and mixtures thereof.

The horticultural spray oils used as carrier with which this invention is concerned have a minimum gravity API of 27; a viscosity at 40° C. of between 8 and 20 centi-Stokes a boiling point range between about 85° & 775° F. and a minimum unsulfonated residue of 85%. An analysis of two typical oils used in evaluating the present invention is given in Table I.

TABLE I

Typical Properties of Spray Oils Used In The Trials

| | Oil A | Oil B | Alkylate Bottoms |
|---|---|---|---|
| Gravity, °API (ASTM D-1250) | 32.6 | 35.2 | 53.7 |
| Flash Point (COC), °F. (ASTM D-92) | 410 | 395 | 132[a] |
| Viscosity cSt. at 40° C. (ASTM D-445) | 18.9 | 15.7 | — |
| Colour (ASTM D-1500) | L 1.0 | L 0.5 | 27[b] |
| Pour Point, °F. (ASTM D-97) | 0 | 5 | — |
| Ash, Wt. % | 0.001 | 0.001 | — |
| Corrosion Copper Strip, 3 hrs at 212° F. (ASTM D-130) | 1A | 1A | — |
| Neutralization Number, mg. KOH/g | 0.03 | 0.04 | — |
| Unsulphonated Residue, Vol. % (ASTM D-483) | — | 94.2 | — |
| F.I.A. | | | |
| Saturates, Vol. % | — | — | 98.5 |
| Aromatics, Vol. % | — | — | 1.5 |
| Olefins, Vol. % | — | — | Nil |
| Distillation, °F. | | | |
| IBP | — | 637 | 352 |
| 10% Recovery | — | 675 | 363 |
| 90% Recovery | — | 729 | 410 |
| FBP | — | 745 | 514 |

[a]Tag.
[b]Say.

In the practice of the invention various blends of the spray oils (Table I) normally used in low volume applications were mixed with suitable blending equipment with the desired amounts of a zinc dialkyldithiophosphate mixture wherein the dialkyl radical ranges from $C_3$ to $C_8$. This mixture a commercially available product is referred to hereinbelow as "the Additive".

It is prepared by reacting about 2.7 moles of an alcohol mixture consisting of about 50 percent primary heptanes ($C_7$) 20% secondary heptanols, 10 percent hexanols ($C_6$) 10% octanols, 5% butanols together with 5 percent of minor alkanols components and about 2.3 moles of isopropanol with 1 mole of $P_2S_5$. The zinc salt is then made by reacting the resulting dialkyldithiophosphoric acid with an excess of zinc oxide.

At relatively high concentrations, foliar applications of the Additive even in a non-phytotoxic light spray oil may be phototoxic. This phenomenon was investigated in Trials Nos. 13/77 and 16/77. The study also enabled the determination of an optimum Additive level safe for use in mixtures with the heavier coventional low volume spray oils as employed in Trials No. 5/77. Corn seedlings (2/pot in Trial No. 13/77 and 3/pot in Nos. 5/77 and 16/77 respectively) grown in vermiculite, peatmoss and sand mixture contained in plastic pots were used as the test crop. A simple randomised block design was employed for each trial in which the spray oil/Additive mixture were applied twice to the plants by either leaf smear or foliar spray. Foliar spraying (3 ml/3 pots/i.e. 9 plants) was employed in Trial No. 5/77, while the leaf smearing technique was used in Trials Nos. 13/77 and 16/77 respectively. The first treatment application was made 7 or 8 days after the corn seeds were sown and the second 7 or 8 days later. When the smearing technique was used, only the newly emerged leaves were treated during the second treatment application. Therefore, the ventral side of each leaf was in fact smeared once with cotton wool soaked in the oil and/or oil solutions. A phytotoxic assessment of the foliage was made the day after each treatment application. Seven days after the last treatment application, the leaves were measured and the above-ground parts of the seedling harvested to determine the fresh and dry tissue weights.

Trial No. 16/77 is therefore a repeat of Trial No. 13/77, the objective of which was to determine the optimum level of the Additive least phytotoxic to the corn seedlings. These trials had 6 treatments which were replicated four times in four blocks. The Additive was screened singularly, being carried in Alkylate Bottoms (Table I) at four concentrations of 0.125%, 0.25%, 0.5% and 1% w/v product. The data of each trial, separately and combined, were computed, and the results are presented in Tables II to IV. In each trial and for their combined data, the seedling growth was increasingly restricted when the leaves were smeared with increments of the Additive in the oil solutions. Basis the variance (F) ratio, however, only the phytotoxicity rating was significantly affected by the treatment in Trial No. 13/77. Conversely, all the parameters measured except the leaf number and the nonfunctional leaf area, were significantly influenced by the experimental treatments in Trial No. 16/77 (Table III). With the combined data, the number of seedling leaves and the three leaf area parameters were not significantly affected by the treatments. However, the other growth parameters exhibited significant reaction to the Additive treatments (Table IV).

In Trial No. 5/77, the Additive was screened together with four other antioxidants. This trial had 13 treatments replicated three times in three blocks. The compounds were carried in Oil A and/or Oil B respectively (Table I) at 0.1% w/v product. The spray oil treatments were applied twice by foliar spraying using an artist air brush. The treatment effect was significant on only two (the dry tissue and the phytotoxity score) of the eight growth parameters measured, basis the variance (F) ratio. In fact, the mean dry tissue weight of the untreated seedlings was significantly greater than those of the other treatments except the Additive/Oil B mixture and the neat Oil A (Table V). Also, the mean phytotoxicity rating of the unsprayed seedling was significantly lower than those of the other treatments except the Additive, Topanol and sulfurized sperm oil carried in Oil B respectively.

It can be concluded from these results that (1) the optimum concentration of the Additive consistent with plant safety lies between 0.25% and 0.1% w/v product; and (2) the Additive of the invention at a low concentration (0.1% w/v product) was less phytotoxic to corn seedlings than Butylzimate and Rokon.

TABLE II

EVALUATION OF ADDITIVE (TRIAL-13/77): MEAN TREATMENT EFFECT ON THE GROWTH OF CORN SEEDLING

| | | | SEEDLING GROWTH MEASUREMENT | | | | | |
|---|---|---|---|---|---|---|---|---|
| | | Height | Weight In Gms. | | No. of | Leaf Area (cm2) | | | Phytotoxicity |
| | Treatment | (cm) | (Fresh) | (Dry) | Leaves | Non-functional | Functional | Total | Score* |
| 1 | Control | 18.2 | 14.3 | 1.68 | 14.8 | 13.0 | 1220.7 | 1233.7 | 0.0 |
| 2 | Alkylate Bottoms | 17.9 | 14.1 | 1.50 | 13.8 | 30.3 | 1195.0 | 1225.3 | 0.1 |
| 3 | Additive/Alkylate Bottoms-0.125% w/v. | 18.4 | 13.7 | 1.65 | 15.0 | 33.5 | 1252.5 | 1285.9 | 1.0 |
| 4 | Additive/Alkylate Bottoms-0.25% w/v. | 17.4 | 13.0 | 1.73 | 15.0 | 24.6 | 1216.0 | 1240.6 | 1.6 |
| 5 | Additive/Alkylate Bottoms-0.5% w/v. | 17.2 | 11.9 | 1.53 | 14.8 | 9.3 | 1169.8 | 1179.1 | 2.8 |
| 6 | Additive/Alkylate Bottoms 1% w/v. | 16.5 | 10.2 | 1.30 | 15.5 | 27.6 | 1141.5 | 1169.1 | 3.0 |
| | S.E. | 1.10 | 1.30 | 0.128 | 0.68 | 7.14 | 109.63 | 112.83 | 0.26 |
| | C.V. % | 12.5 | 20.3 | 16.37 | 9.2 | 62.0 | 18.3 | 18.46 | 37.08 |

*0 = none; 1 = slight; 2 = moderate; 3 = severe.
S.E. = Standard error of a difference between treatment means.
C.V. = Coefficient of variation.

TABLE III

EVALUATION OF ADDITIVE (TRIAL 16/77): MEAN TREATMENT EFFECT ON THE GROWTH OF CORN SEEDLING

| | | | SEEDLING GROWTH MEASUREMENT | | | | | |
|---|---|---|---|---|---|---|---|---|
| | | Height | Weight In Gms. | | No. of | Leaf Area (cm2) | | | Phytotoxicity |
| | Treatment | (cm) | (Fresh) | (Dry) | Leaves | Non-functional | Functional | Total | Score* |
| 1 | Control | 18.9 | 11.1 | 1.33 | 21.8 | 30.1 | 1509.6 | 1539.7 | 0.0 |
| 2 | Alkylate Bottoms | 18.9 | 11.2 | 1.33 | 22.0 | 24.8 | 1575.4 | 1600.2 | 0.0 |
| 3 | Additive/Alkylate Bottoms-0.125% w/v | 18.2 | 9.9 | 1.13 | 22.0 | 13.6 | 1536.0 | 1549.5 | 0.1 |
| 4 | Additive/Alkylate Bottoms-0.25% w/v | 17.3 | 10.6 | 1.20 | 21.8 | 24.3 | 1414.9 | 1439.2 | 1.0 |
| 5 | Additive/Alkylate Bottoms-0.5% w/v | 16.4 | 7.8 | 0.90 | 22.0 | 36.0 | 1351.7 | 1387.7 | 2.6 |
| 6 | Additive/Alkylate Bottoms-1% w/v | 15.9 | 7.5 | 0.82 | 22.3 | 21.0 | 1208.1 | 1229.1 | 3.0 |
| | Standard S.E. | 0.49 | 0.49 | 0.069 | 0.34 | 6.77 | 49.05 | 48.57 | 0.07 |
| | C.V. % | 5.5 | 10.1 | 12.38 | 3.1 | 54.3 | 6.8 | 6.66 | 12.40 |

*0 = none; 1 = slight; 2 = moderate; 3 = severe.

TABLE IV

EVALUATION OF ADDITIVE (TRIAL-13/77 AND 16/77): MEAN TREATMENT EFFECT ON THE GROWTH OF CORN SEEDLING

| | | | SEEDLING GROWTH MEASUREMENT | | | | | |
|---|---|---|---|---|---|---|---|---|
| | | Height | Weight In Gms. | | No. of | Leaf Area (cm2) | | | Phtotoxicity |
| | Treatment | (cm) | (Fresh) | (Dry) | Leaves | Non-functional | Functional | Total | Score* |
| 1 | Control | 18.6 | 12.7 | 1.50 | 18.3 | 21.6 | 1365.1 | 1386.7 | 0.0 |

TABLE IV-continued
EVALUATION OF ADDITIVE (TRIAL-13/77 AND 16/77): MEAN TREATMENT EFFECT ON THE GROWTH OF CORN SEEDLING

| | | SEEDLING GROWTH MEASUREMENT | | | | | | |
|---|---|---|---|---|---|---|---|---|
| | | Height | Weight In Gms. | | No. of | Leaf Area (cm2) | | | Phtotoxicity |
| | Treatment | (cm) | (Fresh) | (Dry) | Leaves | Non-functional | Functional | Total | Score* |
| 2 | Alkylate Bottoms | 18.4 | 12.7 | 1.41 | 17.0 | 27.5 | 1385.2 | 1412.7 | 0.0 |
| 3 | Additive/Alkylate Bottoms-0.125% w/v | 18.3 | 11.8 | 1.39 | 18.5 | 23.5 | 1394.2 | 1417.7 | 0.5 |
| 4 | Additive/Alkylate Bottoms-0.25% w/v | 17.3 | 11.8 | 1.46 | 18.4 | 24.4 | 1315.4 | 1339.9 | 1.3 |
| 5 | Additive/Alkylate Bottoms-0.5% w/v | 16.8 | 9.8 | 1.21 | 18.4 | 22.6 | 1260.7 | 1283.4 | 2.7 |
| 6 | Additive/Alkylate Bottoms-1.0% w/v | 16.2 | 8.8 | 1.06 | 18.9 | 24.3 | 1174.8 | 1199.1 | 3.0 |
| | Standard S.E. | 0.53 | 0.66 | 0.074 | 0.41 | 3.94 | 62.70 | 63.73 | 0.14 |
| | C.V. % | 8.6 | 16.5 | 15.64 | 6.4 | 46.4 | 13.5 | 13.45 | 31.54 |

*0 = none; 1 = slight; 2 = moderate; 3 = severe.

TABLE V
ANTI-OXIDANT IN OILS PHYTOTOXICITY TRIAL (5/77): MEAN TREATMENT EFFECT ON GROWTH OF CORN SEEDLINGS

| | | SEEDLING GROWTH MEASUREMENT | | | | | | |
|---|---|---|---|---|---|---|---|---|
| | | Height | Weight In Grm. | | No. of | Leaf Area (cm2) | | | Phytotoxicity |
| | Treatment | (cm) | (Fresh) | (Dry) | Leaves | Non-functional | Functional | Total | Score* |
| 1 | Control | 23.8 | 25.5 | 2.63 | 25.3 | 21.4 | 3262.6 | 3283.9 | 0.0 |
| 2 | Oil A | 21.5 | 22.4 | 2.47 | 25.3 | 41.3 | 3076.8 | 3118.1 | 1.1 |
| 3 | Oil B | 24.2 | 21.8 | 2.20 | 26.0 | 28.3 | 2988.4 | 3016.7 | 0.8 |
| 4 | Topanol A/Oil A | 21.8 | 21.4 | 2.23 | 25.7 | 76.2 | 3074.4 | 3150.5 | 0.9 |
| 5 | Topanol A/Oil B | 23.4 | 22.6 | 2.33 | 24.3 | 31.8 | 3026.1 | 3057.9 | 0.5 |
| 6 | Rokon /Oil A | 21.8 | 19.9 | 1.93 | 24.3 | 65.6 | 2634.5 | 2700.1 | 1.0 |
| 7 | Rokon/Oil B | 22.2 | 21.5 | 2.13 | 24.7 | 49.9 | 2952.4 | 3002.2 | 0.9 |
| 8 | Butylzimate/Oil A | 21.2 | 20.8 | 2.30 | 24.3 | 70.7 | 2901.3 | 2972.0 | 0.9 |
| 9 | Butylzimate/Oil B | 23.5 | 21.9 | 2.17 | 24.7 | 19.7 | 3011.7 | 3031.4 | 0.7 |
| 10 | Sulfurized Sperm Oil/ Oil A | 21.2 | 22.2 | 2.27 | 25.3 | 54.4 | 3018.5 | 3135.9 | 0.7 |
| 11 | Sulfurized Sperm Oil/ Oil B | 23.9 | 20.8 | 2.23 | 25.3 | 26.4 | 3119.2 | 3145.6 | 0.5 |
| 12 | Additive Oil A | 22.1 | 22.9 | 2.20 | 24.7 | 52.0 | 3227.3 | 3279.3 | 0.9 |
| 13 | Additive Oil B | 24.0 | 23.3 | 2.43 | 25.7 | 28.3 | 3164.1 | 3192.4 | 0.5 |
| | S.E.= | 1.17 | 0.99 | 0.104 | 0.65 | 18.35 | 121.77 | 118.11 | 0.16 |
| | C.V.% | 9.0 | 7.7 | 7.94 | 4.5 | 73.0 | 6.9 | 6.63 | 39.11 |

Topanol A = 2,4-dimethyl-6-t-butylphenol
Rokon = 2-Mercaptobenzothiazole
Butylzimate = Zinc dibutyldithiocarbamate
*0 = none; 1 = slight; 2 = moderate; 3 = severe.

What is claimed is:

1. An agricultural spray oil composition having a minimum gravity API of 27, a viscosity at 40° C. of between 8 and 20 centi-Stokes and a boiling range of 85° to 775° F. and a minimum unsulfonated residue of 85% and containing from 0.1 to 0.25 weight volume percent thereof of at least one zinc dialkyl dithiophosphate wherein the alkyl groups have from 3 to 8 carbon atoms per molecule.

2. The composition according to claim 1 wherein said dithiophosphate consists of the reaction product of about 2.7 moles of an alcohol mixture consisting of about 50 percent primary heptanols, 20 percent secondary heptanols; 10 percent hexanols; 10 percent octanols, 5 percent butanols together with 5 percent of minor alkanol components and 2.3 moles of isopropanol with 1 mole of $P_2S_5$ followed by reacting the resulting dialkyldithiophosphoric acid with an excess of zinc oxide.

3. A process for reducing the phytotoxicity of agricultural spray oils which comprises incorporating therein from 0.10 to 0.25 weight/volume percent thereof of at least one zinc dialkyldithiophosphate wherein the alkyl group ranges from $C_3$ to $C_8$.

* * * * *